United States Patent [19]

Birkmayer

[11] Patent Number: 5,668,114
[45] Date of Patent: Sep. 16, 1997

[54] NADH AND NADPH PHARMACEUTICALS FOR TREATING HYPERTENSION

[75] Inventor: Joerg G. D. Birkmayer, Vienna, Austria

[73] Assignee: Birkmayer Pharmaceuticals, New York, N.Y.

[21] Appl. No.: 646,898

[22] Filed: May 8, 1996

[51] Int. Cl.$^6$ ............................................. A61K 31/70
[52] U.S. Cl. ........................................... 514/52; 514/46
[58] Field of Search ........................... 514/52, 46, 356

[56] References Cited

U.S. PATENT DOCUMENTS

| | | | |
|---|---|---|---|
| 4,497,826 | 2/1985 | Narabayashi et al. | 514/567 |
| 4,970,200 | 11/1990 | Birkmayer et al. | 514/52 |
| 5,019,561 | 5/1991 | Birkmayer et al. | 514/52 |
| 5,037,821 | 8/1991 | Horovitz | 514/211 |
| 5,106,831 | 4/1992 | Fisher et al. | 514/2 |
| 5,332,727 | 7/1994 | Birkmayer | 514/52 |
| 5,444,053 | 8/1995 | Birkmayer | 514/52 |

FOREIGN PATENT DOCUMENTS

| | | |
|---|---|---|
| 2057456 | 7/1992 | Canada. |
| 2135203 | 5/1993 | Canada. |
| 0 256 472 | 2/1988 | European Pat. Off.. |
| 0 496 479 B1 | 7/1992 | European Pat. Off.. |
| 0 615 747 A1 | 9/1994 | European Pat. Off.. |
| 63-301810 | 12/1988 | Japan. |
| 92/0275 | 12/1992 | South Africa. |

*Primary Examiner*—Raymond Henley, III
*Attorney, Agent, or Firm*—Kenyon & Kenyon

[57] ABSTRACT

A method for lowering high blood pressure includes the step of administering the reduced form of nicotinamide adenine dinucleotide (NADH) or the reduced form of nicotinamide adenine dinucleotide phosphate (NADPH) or physiologically compatible salts of NADH and/or NADPH. Patients so treated exhibit a significant reduction of their elevated blood pressure over time. The method is effective in treating hypertension and chronic hypertension.

18 Claims, No Drawings

NADH AND NADPH PHARMACEUTICALS FOR TREATING HYPERTENSION

BACKGROUND OF THE INVENTION

1. Field of the Invention

The invention relates to a pharmaceutical and a method for treating patients with high blood pressure and, more particularly, to the use of reduced forms of nicotinamide adenine dinucleotide (NADH), nicotinamide adenine dinucleotide phosphate (NADPH), and physiologically acceptable salts thereof in the treatment of hypertension.

2. Description of Related Art

Hypertension, a major public health problem, is defined as the condition of having blood pressure (BP) exceeding an upper limit of normality. The upper limit is generally accepted as a systolic BP>140 mg. Hg and/or diastolic BP>90 mg Hg. This perturbation is a major risk factor for cardiovascular diseases (CVD) which account for approximately 50% of mortality beyond age 65.

It is generally accepted that a significant elevation of blood pressure can accelerate the aging process in the circulatory system. During aging, many factors involved in regulating blood pressure can go awry. Therefore it is not surprising that systolic and diastolic blood pressure increase progressively with aging, a phenomenon which is called "age-related hypertension." Hypertension is found in 50% or more of individuals above age 55 years, and 63% of those age 65 to 74 years. The rate is 76% among persons of African origin over 65 years old in the United States. This age-related hypertension, particularly of the diastolic blood pressure, is most likely due to the reduced elasticity of the blood vessels or, even worse, stiffness of the blood vessels. This reduced elasticity may be caused by damage of the muscle layer of the blood vessels. This damage can be caused by radicals from chemicals, radiation or other toxins. Due to this, these endothelial muscles cannot function properly contracting and relaxing when blood pressure demand makes that necessary. The consequence is a higher diastolic blood pressure.

There are numerous substances in use against higher blood pressure such as angiotensin-converting enzyme (ACE) inhibitors, anti-sympaticotonica, beta-blockers, calcium-antagonists, diuretics, vasodilatators and all kinds of combinations. However, all these drugs are synthetic chemical substances which do not occur naturally in the human body. It would be very desirable to discover an endogenous substance which can regulate high blood pressure.

Nicotinamide-adenine-dinucleotide in its reduced form ("NADH") and nicotinamide-adenine-phosphate-dinucleotide in its reduced form ("NADPH") are physiological substances which occur in all living cells including human cells. These substances are cofactors for a variety of enzymes, the majority of which catalyze oxidation-reduction reactions. Prior to recent discoveries as to certain therapeutic properties of these compounds, their principal utility has been as diagnostic tools in clinical biochemistry and as essential components in reaction kits, for example, in measuring lactatdehydrogenase (LDH).

The most important function of NADH is its driving force for cell respiration. When using oxygen, NADH forms water and 3 ATP molecules in accordance with the following formula: $NADH + H^+ + \frac{1}{2} O_2 + 3 \, Pi + 3 \, ATP \rightarrow NAD^+ + 3 \, ATP + 4H_2O$. Thus, with 1 NADH molecule, 3 ATP molecules are obtained which have an energy of approximately 21 kilocalories. This process is called oxidative phosphorylation. The supply of NADH and/or NADPH makes this work much easier for the organism, because it has greater energy reserves as a result.

More recently, NADH and NADPH and pharmaceutically acceptable salts thereof have been shown to be useful in the treatment of Parkinson's Disease. The effectiveness of these agents for this purpose is documented in my U.S. Pat. Nos. 4,970,200 and 5,019,561, the disclosures of which are incorporated herein by reference.

In addition, I have discovered that these substances are effective in the treatment of Morbus Alzheimer (i.e., Alzheimer's Disease), which is the subject of my U.S. Pat. No. 5,444,053.

Prior to my recent discoveries, NADH and NADPH have never been considered for therapeutic use, probably because it was believed that these compounds are rather unstable and, hence, not capable of being absorbed by the intestines of the human body. It would have been expected that these substances would be hydrolized in the plasma within a few seconds.

However, studies performed recently using NADH and NADPH demonstrate that these assumptions are incorrect. When NADH and NADPH were applied intravenously to patients with Parkinson's disease, a remarkable beneficial effect was observed which lasted at least 24 hours. See U.S. Pat. Nos. 4,970,200 and 5,019,561. This indicates that NADH and NADPH are not rapidly degraded in the plasma and blood.

SUMMARY OF THE INVENTION

It is an object of the invention to provide a new drug and method which is effective in lowering the blood pressure of patients suffering from hypertension.

In accordance with the invention, the reduced form of nicotinamide adenine dinucleotide (NADH), nicotinamide adenine dinucleotide phosphate (NADPH), or physiologically acceptable salts or derivatives of NADH and NADPH are administered to patients with hypertension. Daily single doses of between 1 and 50 mg of NADH or NADPH, or mixtures thereof, may be used for effective treatment. Preferred doses are from 5 to 15 mg in the case of NADH and from 1 to 5 mg in the case of NADPH.

The administration of these endogenous substances as a pharmaceutical leads to a surprising therapeutic result in persons with high blood pressure without any side effects. In patients exhibiting hypertension a significant reduction of blood pressure is achieved by 3–4 weeks after treatment with NADH or NADPH. Without intending to be bound by any theory, it is believed that NADH and NADPH give back to the endothelial muscles the energy to contract and relax in the appropriate and demanded way, thereby resulting in a reduced diastolic blood pressure.

DETAILED DESCRIPTION OF THE INVENTION

When NADH, NADPH, or their physiologically tolerable salts are employed in accordance with the invention, they can be manufactured in the usual way with pharmaceutically acceptable fillers, or they can be incorporated for use as drugs into conventional galenic formulations for oral, parenteral, rectal, sublingual and nasal applications. The preparations can exist: in a solid form as tablets, capsules or coated tablets; in liquid form as a solution, suspension, spray or emulsions; in the form of suppositories, as well as in formulations having a delayed release of the active substances.

Suitable oral forms of NADH and NADPH which can be used in the practice of this invention are described in my U.S. Pat. No. 5,332,727, the disclosure of which is incorporated herein by reference. Both NADH and NADPH are very unstable at pHs below 7 which prevail within the confines of the stomach. Therefore, when used in oral form, these substances must be coated with an acid stable protective film so that they can survive the stomach environment for subsequent absorption by the intestine. Suitable acid stable coatings are known in the art and can be applied by a conventional coating process after the active ingredients are formed into a tablet or capsule. Examples of suitable coatings are: cellulose acetate phthalate; polyvinylacetate phthalate; hydroxyl-propyl-methyl cellulose phthalate; methacryllic acid copolymers; fat-wax; shellac; zein; aquacoating; and surerelease. Another possibility for the coating is a solution of a phthalate and a lack dry substance in isopropanol. An example of a suitable lack dry substance is sold under the name EUDRAGIT™ by Rohm Pharma. Alternatively, a protein coating in an aqueous medium may be applied. However, a sugar-coating should not be used because it will destabilize NADH.

Although NADH and/or NADPH may be used by themselves in pure form (they are quite stable in compressed form when protected from light), it is preferred that they be combined in a galenic formulation with a stabilizer which is effective to inhibit oxidation of NADH and NADPH to the inactive oxidized forms $NAD^+$ and $NADP^+$, respectively. Most preferably, the NADH and/or NADPH is combined with both a stabilizer and a filler. It has been found that the following stabilizers are effective in inhibiting oxidation to the inactive $NAD^+$ and $NADP^+$ and result in the greatest shelf stability for NADH and NADPH: $NaHCO_3$; ascorbic acid and sodium ascorbate; tocopherols and tocopherolacetates; polyvinylpyrolidone ("PVP") 12 (12 representing the molecular weight 12,000); PVP 25; PVP 40; PVP PF 17 (meaning polymer having a molecular weight from 17,000) and PVP PF 60. NADH/NADPH formulations containing such stabilizers are stable for up to two years. Other various stabilizers will become apparent to those skilled in the art.

Suitable fillers for use with NADH and NADPH include: mannitol, microcrystalline cellulose, carboxymethyl cellulose; and dibasic calcium phosphate. Other suitable fillers will become apparent to those skilled in the art. Lactose should be avoided as a. filler because it reacts with NADH.

In general, a preferred formulation will include about 3 to 10% by weight NADH and/or NADPH; about 1 to 10% by weight stabilizer; and a balance of filler. Such a formulation, after being compressed into a pill or tablet and coated, is stable for over 24 months.

The NADH and/or NADPH, together with the optional stabilizer and filler, may be formed into tablets, capsules, microtablets or micropellets by processes known in the art of pill manufacturing. Tablets may be formed either by direct compression or by granulation followed by compression. Capsules may be formed by blending the components and subsequently filling capsules with the blend using conventional automatic filling equipment. Microtablets may be formed by compressing powdered or granulated components into, e.g., 2 mm diameter tablets.

In the case of direct compression into tablets, a particularly preferred formulation is: NADH 5%, sodium ascorbate 5%, magnesium stearate 3%, talc 4%, silicon dioxide 1%, and mannitol 82%.

In the case of capsules, a particularly preferred formulation is: NADH 5%, sodium ascorbate 5%, polyvinyl- pyrolidone (PVP) 5%, microcrystalline cellulose 77%, magnesium stearate 3%, alpha-tocopherolacetate 1%, talc 3%, and silicon dioxide 1%.

Suitable physiologically acceptable salts of the coenzymes NADH and NADPH include all known physiologically acceptable acidic and basic salt-forming substances, for example: inorganic acids such as, for example, hydrochloric acids, sulfuric acid, phosphoric acid; organic acids such as, for example, aliphatic or aromatic carboxylic acids, e.g., formic acid, acetic acid, succinic acid, lactic acid, malic acid, tartaric acid, citric acid, maleic acid, phenylacetic acid, benzoic acid, salicylic acid or ascorbic acid; or alkali metal hydroxides or alkaline earth metal hydroxides or salts.

For nasal administration, the NADH and/or NADPH may be taken in the form of a liquid spray or a powder spray, a gel, an ointment, an infusion, an injection or nose drops. Examples of liquid spray formulations are:

| NADH Liquid Spray Formulation | NADPH Liquid Spray Formulation |
| --- | --- |
| NADH 12 mg and Sodium ascorbate 36 mg, dissolved in 1 ml deionized water | NADPH 2.5 mg and Sodium ascorbate 36 mg, dissolved in 1 ml deionized water |
| 1 Spray dose is 0.13 ml containing 1.5 mg NADH | 1 Spray dose is 0.13 ml containing 0.32 mg NADPH |

For a powder spray, the NADH is simply ground into a fine powder and atomized from a spray bottle. Preferably, pure NADH is used for the powder spray, however, it can be used in conjunction with a filler, such as mannitol, as described below. The NADH which is inhaled through the nasal passages is absorbed by the mucosa of the nose and travels to the brain through the olfactory neural pathway. NADH administered in this manner has the same therapeutic effects as the oral form described above.

Thus, in accordance with the invention, the NADH may be administered to the nasal cavity of a patient afflicted with hypertension or symptoms thereof. The NADH (and/or NADPH) may be applied alone or in combination with other substances, for example, a pharmaceutically acceptable carrier or an agent that facilitates the transfer of the NADH through the nasal mucosa. The NADH is administered intranasally as a powder, spray, gel, ointment, infusion, injection or nose drops. The NADH is delivered to the nasal cavity. It is preferred that the NADH be delivered to the olfactory area in the upper third of the nasal cavity, and particularly to the olfactory neuroepithelium in order to promote transport of the NADH into the peripheral olfactory neurons rather than the capillaries within the respiratory epithelium. It is preferred that the transport of NADH to the brain be by means of the nervous system rather than the circulatory system so that the blood-brain barrier from the bloodstream into the brain is circumvented. However, good results can also be obtained through the bloodstream.

Surprisingly, it has been discovered that NADH (and NADPH) is capable of at least partially dissolving in the fluids that are secreted by the mucous membrane which surrounds the cilia of the olfactory receptor cells of the olfactory epithelium so that it may be absorbed into the olfactory neurons. The NADH may be combined with a carrier or other substance that fosters dissolution within nasal secretions, such as the ganglioside GM-1 or the phospolipid phosphatidylserine, or emulsifiers such as polysorbate 80. The NADH may be combined with micelles comprised of lipophilic substances which modify the permeability of the nasal membrane to enhance absorption of the NADH. Lipophilic micelles which are effective for this purpose include the gangliosides, the phospholipids and phosphatidylserine. Alternatively, the NADH may be combined with liposomes to enhance absorption of the NADH into the olfactory system.

I have also discovered that NADH (and/or NADPH) is effective in treating high blood pressure and hypertension when administered sublingually. Sublingual resorption of NADH achieves very fast results. The NADH is merely placed underneath the tongue and resorbed. Unlike the oral form of NADH described above, a sublingual form should not be coated with an acid stable protective coating.

It has also been discovered that good results are obtained when NADH (and/or NADPH) is administered rectally. NADH may be administered rectally in the form of suppositories. A suitable suppository formulations are:

| NADH Suppository Formulation | | NADPH Suppository Formulation | |
| --- | --- | --- | --- |
| NADH | 5 mg | NADPH | 2 mg |
| Sodium ascorbate | 20 mg | Sodium ascorbate | 20 mg |
| Suppository mass | 2475 mg | Suppository mass | 2478 mg |
| (Massa Novata BC, Henkel Inc) | | (Maasa Novata BC, Henkel Inc) | |

For all forms of administration (oral, sublingual, rectal, intravenous and nasal), the NADH or NADPH, or both, may be administered alone. If necessary or desired, the NADH and NADPH can also be used in combination with other active antihypertensive agents, for example, ACE inhibitors, beta-blockers, and calcium antagonists such as Nifedipin™. NADH, NADPH or their physiologically compatible salts can be manufactured in the usual manner with pharmaceutically acceptable auxiliaries and carrier materials.

It is believed that NADH and NADPH are effective in alleviating hypertension because they provide needed energy to the blood vessel endothelial muscles which enhances the ability of these muscles to properly contract and relax as necessary, thereby resulting in a reduced diastolic blood pressure.

Specific preferred embodiments of the invention will now be described with reference to the following examples which should be regarded in an illustrative, rather than a restrictive, sense. It was surprising and completely unexpected to discover that NADH and NADPH are effective in lowering the blood pressure in patients with hypertension.

EXAMPLE I

A 62 year old male patient showed a systolic blood pressure of 160 mm Hg and a diastolic blood pressure of 95, even after long-term treatment with beta-blockers or calcium antagonists. The patient was diagnosed as suffering from persistent hypertension. The patient was treated by administering 10 mg of NADH daily for one month. Beta-blockers and calcium antagonists were also continued over that period. After the treatment, an examination revealed that the patient's systolic blood pressure went down to 140 and a diastolic blood pressure to 85. The NADH treatment was subsequently continued and the patient's condition regarding blood pressure continued to remain the same. No side effects were observed nor did the patient complain of any.

EXAMPLE II

A female patient, 53 years of age, had a systolic blood pressure of 180 and a diastolic blood pressure of 100 for several years. A number of antihypertensive drugs, including ACE inhibitors, calcium antagonists and diuretics, had been given to this patient in an attempt to abate her high blood pressure. However, these drugs and a combination of them could not reduce the blood pressure to normal values. A physical examination led to a diagnosis of chronic hypertension. The patient was then administered 15 mg NADH daily orally for one month and her other antihypertensive medication was discontinued. An examination after this NADH treatment period showed a systolic blood pressure of 150 and a diastolic pressure of 90. The NADH treatment was subsequently continued and the patient's blood pressure remained fairly constant over the prolonged treatment period. No side effects were observed nor did the patient complain of any.

EXAMPLE III

A male patient, 67 years old, had a systolic blood pressure of 185 and a diastolic blood pressure of 100. He was treated for about 6 years with conventional antihypertensive drugs, including beta-blockers, calcium antagonists, diuretics and ACE inhibitors. With this treatment the patient's systolic and diastolic blood pressure could be decreased to 160 and 95, respectively. Hence, the patient was diagnosed as having refractory hypertension. The patient was administered 10 mg of NADH orally once a day for 4 weeks, in addition to his original medication of beta-blockers and diuretics. After 2 weeks, the systolic blood pressure in this patient went down to 140 and the diastolic blood pressure was found to be 85. At this time, the NADH treatment was discontinued, whereupon the patient's systolic blood pressure increased again to 170 and the diastolic blood pressure was 95. After a four week observation period the patient received again 10 mg of NADH orally per day. After 5 days the systolic blood pressure came down to 150 and the diastolic blood pressure came down to 85. The NADH treatment was continued for more than one year and the blood pressure value remained fairly constant over that period of time.

EXAMPLE IV

A 60 year old male patient was diagnosed with chronic hypertension, exhibiting a systolic blood pressure of 190 and a diastolic blood pressure of 110. The patient had already been treated with a variety of conventional antihypertensive drugs, including ACE inhibitors, beta-blockers, calcium antagonists and diuretics, which did not lead to a significant decrease in blood pressure. 10 mg of NADPH was administered intravenously every other day for a period of 2 weeks. After the NADPH therapy the patient exhibited a systolic blood pressure of 145 and a diastolic blood pressure of 90. This treatment was continued for a period of 6 weeks, during which time the patient's blood pressure values, systolic as well as diastolic, remained fairly stable.

EXAMPLE V

A 70 year old female patient exhibited systolic blood pressure of 200 and a diastolic blood pressure of 110. Treatment with conventional antihypertensive drugs, including calcium antagonists, vasodilatators and beta-blockers did not lead to a considerable reduction of the blood pressure. The patient was diagnosed as having chronic hypertension.

5 mg of NADPH was administered intravenously every other day for 2 weeks. The prior conventional medication was also continued. After these 2 weeks the patient's systolic blood pressure came down to 170 and the diastolic blood pressure to 90. The treatment was then prolonged for another four weeks and the decrease in blood pressure was maintained during the extended therapy. No side effects were observed. The patient stated that she felt much better as the uncomfortable symptoms and side effects of high blood pressure have disappeared. She did not report any side effects nor were any side effects observed.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than a restrictive sense.

What is claimed is:

1. A method of treating high blood pressure, comprising the step of orally administering to a patient suffering from hypertension an effective amount of NADH or NADPH, or a physiologically compatible salt of NADH or NADPH, said NADH or NADPH or salt being coated with an acid stable protective film.

2. The method according to claim 1 wherein the NADH or NADPH is administered in a dose of from 1 mg to 40 mg.

3. The method according to claim 2 wherein NADH is administered in a dose of from 5 mg to 10 mg.

4. The method according to claim 2 wherein NADPH is administered in a dose of from 1 mg to 10 mg.

5. The method according to claim 2 wherein said dose is administered every 24 hours.

6. The method according to claim 3 wherein said dose is administered every 24 hours.

7. The method according to claim 4 wherein said dose is administered every 24 hours.

8. The method according to claim 1, further comprising the step of administering to said patient an anti-hypertension drug selected from the group consisting of angiotension-converting enzyme inhibitors, beta-blockers, anti-sympaticotonica, calcium antagonists, diuretics and vasodilators.

9. A method of lowering systolic blood pressure in a person having a systolic blood pressure of greater than 140 mm Hg, comprising the step of orally administering to said person an amount of NADH or NADPH, or a physiologically acceptable salt of NADH or NADPH, which is effective to lower said systolic blood pressure, said NADH or NADPH or salt being coated with an acid stable protective film.

10. The method according to claim 9, further comprising the step of administering to said patient an anti-hypertension drug selected from the group consisting of angiotension-converting enzyme inhibitors, beta-blockers, anti-sympaticotonica, calcium antagonists, diuretics and vasodilators.

11. A method of lowering diastolic blood pressure in a person having a diastolic blood pressure of greater than 90 mm Hg, comprising the step of orally administering to said person an amount of NADH or NADPH, or a physiologically acceptable salt of NADH or NADPH, which is effective to lower said diastolic blood pressure, said NADH or NADPH or salt being coated with an acid stable protective film.

12. The method according to claim 11, further comprising the step of administering to said patient an anti-hypertension drug selected from the group consisting of angiotension-converting enzyme inhibitors, beta-blockers, anti-sympaticotonica, calcium antagonists, diuretics and vasodilators.

13. A method of treating high blood pressure, comprising the step of administering to a patient suffering from hypertension an effective amount of NADH or NADPH, or a physiologically compatible salt of NADH or NADPH, wherein said NADH or NADPH or salt is administered intravenously, sublingually, rectally, or to a nasal passage of the patient to result in absorption of the NADH or NADPH or salt into mucosa of the nose.

14. The method according to claim 13 wherein NADH is administered in a dose of from 5 mg to 10 mg.

15. The method according to claim 14 wherein said dose is administered every 24 hours.

16. The method according to claim 13, further comprising the step of administering to said patient an anti-hypertension drug selected from the group consisting of angiotension-converting enzyme inhibitors, beta-blockers, anti-sympaticotonica, calcium antagonists, diuretics and vasodilators.

17. A method of lowering systolic blood pressure in a person having a systolic blood pressure of greater than 140 mm Hg, comprising the step of administering to said person an amount of NADH or NADPH, or a physiologically acceptable salt of NADH or NADPH, which is effective to lower said systolic blood pressure, wherein said NADH or NADPH or salt is administered intravenously, sublingually, rectally, or to a nasal passage of the patient to result in absorption of the NADH or NADPH or salt into mucosa of the nose.

18. A method of lowering diastolic blood pressure in a person having a diastolic blood pressure of greater than 90 mm Hg, comprising the step of administering to said person an amount of NADH or NADPH, or a physiologically acceptable salt of NADH or NADPH, which is effective to lower said diastolic blood pressure, wherein said NADH or NADPH or salt is administered intravenously, sublingually, rectally, or to a nasal passage of the patient to result in absorption of the NADH or NADPH or salt into mucosa of the nose.

* * * * *